(12) United States Patent
Wang et al.

(10) Patent No.: US 11,845,741 B2
(45) Date of Patent: Dec. 19, 2023

(54) PILOCARPINE IONIC LIQUIDS FOR TREATMENT OF GLAUCOMA

(71) Applicant: VIRGINIA COMMONWEALTH UNIVERSITY INTELLECTUAL PROPERTY FOUNDATION, Richmond, VA (US)

(72) Inventors: Juan Wang, Richmond, VA (US); Hu Yang, Glen Allen, VA (US)

(73) Assignee: VIRGINIA COMMONWEALTH UNIVERSITY INTELLECTUAL PROPERTY FOUNDATION, Richmond, VA (US)

( * ) Notice: Subject to any disclaimer, the term of this patent is extended or adjusted under 35 U.S.C. 154(b) by 134 days.

(21) Appl. No.: 17/478,187

(22) Filed: Sep. 17, 2021

(65) Prior Publication Data

US 2022/0081425 A1   Mar. 17, 2022

Related U.S. Application Data

(60) Provisional application No. 63/079,527, filed on Sep. 17, 2020.

(51) Int. Cl.
| | |
|---|---|
| *C07D 405/06* | (2006.01) |
| *A61P 27/06* | (2006.01) |
| *A61K 45/06* | (2006.01) |
| *A61K 31/4178* | (2006.01) |
| *A61K 9/00* | (2006.01) |

(52) U.S. Cl.
CPC .......... *C07D 405/06* (2013.01); *A61K 9/0048* (2013.01); *A61K 31/4178* (2013.01); *A61K 45/06* (2013.01); *A61P 27/06* (2018.01)

(58) Field of Classification Search
CPC ..... C07D 405/06; A61P 27/06; A61K 9/0048; A61K 31/4178; A61K 45/06
See application file for complete search history.

(56) References Cited

PUBLICATIONS

Ben-Bassat; J. Med. Chem. 1971, 14, 11, 1066-1069. https://doi.org/10.1021/jm00293a011 (Year: 1971).*
Ben-Bassat; J. Med. Chem. 1976, 19, 928-933. https://doi.org/10.1021/jm00229a014 (Year: 1976).*
Huang; Soft Matter, 2011, 7, 8392-8400. https://doi.org/10.1039/C1SM05759F (Year: 2011).*
Wang; ACS Pharmacol. Transl. Sci. 2022, 5, 9, 752-760. https://doi.org/10.1021/acsptsci.2c00024 (Year: 2022).*
Gould, P. L. Salt selection for basic drugs. Int. J. Pharm. 1986, 33 (1), 201-217.
Semin, D. J.; Jona, J.; Peterson, M. L.; Zanon, R. Salt screening and selection. Burger's Medicinal Chemistry and Drug Discovery, 2010, 381-400.
Bastin, R. J.; Bowker, M. J.; Slater, B. J. Salt selection and optimisation procedures for pharmaceutical new chemical entities. Org. Process Res. Dev. 2000, 4 (5), 427-435.
Elder, D. P.; Snodin, D. J. Drug substances presented as sulfonic acid salts: overview of utility, safety and regulation. J. Pharm. Pharmacol. 2009, 61 (3), 269-278.
Sarma, B.; Chen, J.; Hsi, H.-Y.; Myerson, A. S. Solid forms of pharmaceuticals: polymorphs, salts and cocrystals. Korean J. Chem. Eng. 2011, 28 (2), 315-322.
Shamshina, J. L.; Kelley, S. P.; Gurau, G.; Rogers, R. D. Chemistry: develop ionic liquid drugs. Nature 2015, 528 (7581), 188-189.
Rogers, R. D.; Seddon, K. R. Ionic liquids—solvents of the future? Science 2003, 302 (5646), 792-793.
Seddon, K. R. A taste of the future. Nat. Mater. 2003, 2 (6), 363-365.
Hough, W. L.; Smiglak, M.; Rodríguez, H.; Swatloski, R. P.; Spear, S. K.; Daly, D. T.; Pernak, J.; Grisel, J. E.; Carliss, R. D.; Soutullo, M. D.; Davis, J. J. H.; Rogers, R. D. The third evolution of ionic liquids: active pharmaceutical ingredients. New J. Chem. 2007, 31 (8), 1429-1436.
Balk, A.; Holzgrabe, U.; Meinel, L. 'Pro et contra' ionic liquid drugs—challenges and opportunities for pharmaceutical translation. Eur. J. Pharm. Biopharm. 2015, 94, 291-304.
Balk, A.; Wiest, J.; Widmer, T.; Galli, B .; Holzgrabe, U.; Meinel, L. Transformation of acidic poorly water soluble drugs into ionic liquids. Eur. J. Pharm. Biopharm. 2015, 94, 73-82.
Dobler, D.; Schmidts, T.; Klingenhöfer, I.; Runkel, F. Ionic liquids as ingredients in topical drug delivery systems. Int. J. Pharm. 2013, 441 (1), 620-627.
Ferraz, R.; Branco, L. C.; Prudêncio, C.; Noronha, J. P.; Petrovski, Ž. Ionic liquids as active pharmaceutical ingredients. ChemMedChem 2011, 6 (6), 975-985.
Kumar, V.; Malhotra, S. V. Ionic liquids as pharmaceutical salts: a historical perspective. Ionic Liquid Applications: Pharmaceuticals, Therapeutics, and Biotechnology, ACS Symposium Series 2010, 1038, 1-12.
Marrucho, I. M.; Branco, L. C.; Rebelo, L. P. N. Ionic liquids in pharmaceutical applications. Annu. Rev. Chem. Biomol. Eng. 2014, 5 (1), 527-546.
Stoimenovski, J.; MacFarlane, D. R.; Bica, K.; Rogers, R. D. Crystalline vs. ionic liquid salt forms of active pharmaceutical ingredients: a position paper. Pharm. Res. 2010, 27 (4), 521-526.
Davis, J. H.; Forrester, K. J.; Merrigan, T. Novel organic ionic liquids (OILs) incorporating cations derived from the antifungal drug miconazole. Tetrahedron Lett. 1998, 39 (49), 8955-8958.
Monti, D.; Egiziano, E.; Burgalassi, S.; Chetoni, P.; Chiappe, C.; Sanzone, A.; Tampucci, S. Ionic liquids as potential enhancers for transdermal drug delivery. Int. J. Pharm. 2017, 516 (1), 45-51.
Babighian, S. Medical antiglaucomatous therapy. Glaucoma Surgery, Springer 2018; 97-98.
Flocks, M.; Zweng, H. C. Studies on the mode of action of pilocarpine on aqueous outflow. Am. J. Ophthalmol. 1957, 44, 380-386.
Skaat, A.; Rosman, M. S.; Chien, J. L.; Mogil, R. S.; Ren, R.; Liebmann, J. M.; Ritch, R.; Park, S. C. Effect of pilocarpine hydrochloride on the schlemm canal in healthy eyes and eyes with open-angle glaucoma. JAMA Ophthalmol. 2016, 134 (9), 976-981.

(Continued)

*Primary Examiner* — Daniel R Carcanague
(74) *Attorney, Agent, or Firm* — Meunier Carlin & Curfman LLC

(57) ABSTRACT

The present disclosure provides pilocarpine ionic liquid analogs useful in the treatment of ophthalmological disorders such as glaucoma.

20 Claims, 12 Drawing Sheets

(56) References Cited

PUBLICATIONS

Yuan, Q.; Fu, Y.; Kao, W. J.; Janigro D.; Yang, H. Transbuccal delivery of CNS therapeutic nanoparticles: synthesis, characterization, and in vitro permeation studies. ACS Chem. Neurosci. 2011, 2, 676-683.

Katayanagi, H.; Nishikawa, K.; Shimozaki, H.; Miki, K.; Westh, P.; Koga, Y. Mixing schemes in ionic liquid-H2O systems: a thermodunamic study. J. Phys. Chem. B 2004, 108, 19451-19457.

Pilatti, C; M. C. Torre, C. Chiale and M. Spinetto, Drug Development and Industrial Pharmacy, 1999, 25, 801-805.

Fernandes and C. R. Gattass, Journal of Medicinal Chemistry, 2009, 52, 1214-1218.

\* cited by examiner

PILOCARPINE IONIC LIQUIDS FOR TREATMENT OF GLAUCOMA

CROSS-REFERENCE TO RELATED APPLICATIONS

This application claims the benefit of priority to U.S. Provisional Application No. 63/079,527, filed Sep. 17, 2020, the disclosure of which is incorporated herein by reference in its entirety.

STATEMENT REGARDING FEDERALLY SPONSORED RESEARCH OR DEVELOPMENT

This invention was made with government support under Grant No. R01 EY024072 awarded by the National Institutes of Health (NIH). The Government has certain rights in the invention.

TECHNICAL FIELD

This disclosure relates to compounds for the treatment of ophthalmological disorders, and more particularly to pilocarpine ionic liquids useful in the treatment of glaucoma.

BACKGROUND

Glaucoma refers to a group of eye conditions which damage the optic nerve and which can lead to loss of vision. The primary cause of damage to the optic nerve in glaucoma is intraocular pressure (excessive fluid pressure within the eye), which can be the result of various reasons such as blockage of drainage ducts or narrowing or closure of the angle between the iris and cornea. Several classes of medication which decrease intraocular pressure are used in the treatment of glaucoma, usually as eye drops. Miotic agents, such as pilocarpine, are used in the treatment of glaucoma and work by contraction of the ciliary muscle, opening the trabecular meshwork and allowing increased outflow of the aqueous humor. While pilocarpine is typically delivered in its salt forms (either as the chloride or nitrate salt) which exhibit good aqueous solubility, it readily epimerizes in aqueous solution via hydrolytic opening of its lactone moiety. Thus, there is a clear need for new therapeutics that can be used for the treatment of glaucoma.

SUMMARY

The present disclosure provides compounds and compositions which are useful in the treatment of ophthalmological disorders, particularly glaucoma. More specifically, pilocarpine ionic liquid analogs are provided which show improved potency, enhanced stability, cytocompatibility, and permeability compared to presently available pilocarpine formulations.

Thus, in one aspect, a compound of Formula I is provided:

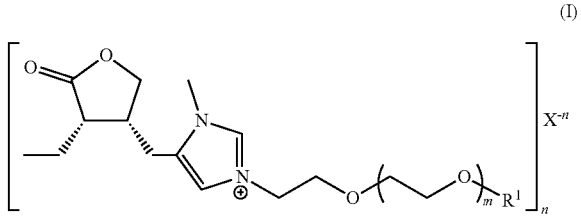

(I)

wherein all variables are as defined herein.

In another aspect, an ophthalmological composition is also provided comprising a compound of Formula I and an ophthalmologically suitable carrier.

In a further aspect, methods for treating glaucoma in a subject are provided comprising administering to the subject a therapeutically effective amount of a compound of Formula I or an ophthalmological composition as described herein.

The details of one or more embodiments of the disclosure are set forth in the accompanying drawings and the description below. Other features, objects, and advantages of the disclosure will be apparent from the description and drawings, and from the claims.

DETAILED DESCRIPTION

Figure 1A:
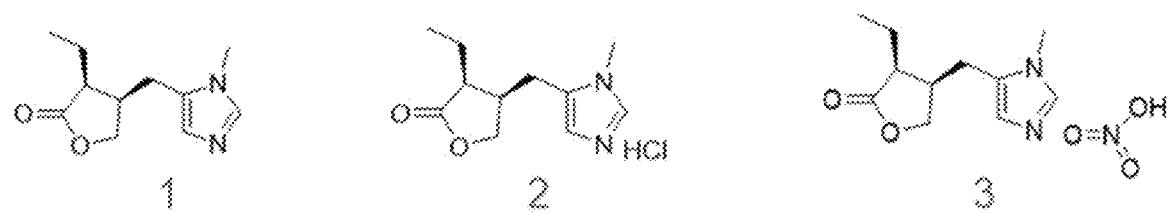
FIG. 1A shows the chemical structure of pilocarpine (1), pilocarpine hydrochloride (2), and pilocarpine nitrate (3).

The following description of the disclosure is provided as an enabling teaching of the disclosure in its best, currently known embodiments. Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As can be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It can be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of."

As used in the specification and the appended claims, the singular forms "a," "an" and "the" include plural referents unless the context clearly dictates otherwise. Thus, for example, reference to "a compound", "a composition", or "a disorder", includes, but is not limited to, two or more such compounds, compositions, or disorders, and the like.

It should be noted that ratios, concentrations, amounts, and other numerical data can be expressed herein in a range format. It can be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it can be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound or composition can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the terms "optional" or "optionally" means that the subsequently described event or circumstance can or cannot occur, and that the description includes instances where said event or circumstance occurs and instances where it does not.

As used interchangeably herein, "subject," "individual," or "patient" can refer to a vertebrate organism, such as a mammal (e.g. human) "Subject" can also refer to a cell, a population of cells, a tissue, an organ, or an organism, preferably to human and constituents thereof.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as glaucoma. The effect can be therapeutic in terms of a partial or complete cure of a disease, condition, symptom or adverse effect attributed to the disease, disorder, or condition. The term "treatment" as used herein can include any treatment of a disorder in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

Compounds are described using standard nomenclature. Unless defined otherwise, all technical and scientific terms used herein have the same meaning as is commonly understood by one of skill in the art to which this invention belongs.

"Alkyl" is a straight chain or branched saturated aliphatic hydrocarbon group. In certain embodiments, the alkyl is $C_1$-$C_2$, $C_1$-$C_3$, or $C_1$-$C_6$ (i.e., the alkyl chain can be 1, 2, 3, 4, 5, or 6 carbons in length). The specified ranges as used herein indicate an alkyl group with length of each member of the range described as an independent species. For example, $C_1$-$C_6$alkyl as used herein indicates an alkyl group having from 1, 2, 3, 4, 5, or 6 carbon atoms and is intended to mean that each of these is described as an independent species and $C_1$-$C_4$alkyl as used herein indicates an alkyl group having from 1, 2, 3, or 4 carbon atoms and is intended to mean that each of these is described as an independent species. When $C_0$-$C_n$alkyl is used herein in conjunction with another group, for example ($C_3$-$C_7$cycloalkyl)$C_0$-$C_4$alkyl, or —$C_0$-$C_4$($C_3$-$C_7$cycloalkyl), the indicated group, in this case cycloalkyl, is either directly bound by a single covalent bond ($C_0$alkyl), or attached by an alkyl chain, in this case 1, 2, 3, or 4 carbon atoms. Alkyls can also be attached via other groups such as heteroatoms, as in —O—$C_0$-$C_4$alkyl($C_3$-$C_7$cycloalkyl). Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane.

A dash ("-") that is not between two letters or symbols is used to indicate a point of attachment for a substituent. For example, —(C=O)NH$_2$ is attached through the carbon of the keto (C=O) group.

As used herein, substantially pure means sufficiently homogeneous to appear free of readily detectable impurities as determined by standard methods of analysis, such as thin layer chromatography (TLC), nuclear magnetic resonance (NMR), gel electrophoresis, high performance liquid chromatography (HPLC) and mass spectrometry (MS), gas-chromatography mass spectrometry (GC-MS), and similar, used by those of skill in the art to assess such purity, or sufficiently pure such that further purification would not detectably alter the physical and chemical properties, such as enzymatic and biological activities, of the substance. Both traditional and modern methods for purification of the compounds to produce substantially chemically pure compounds are known to those of skill in the art. A substantially chemically pure compound may, however, be a mixture of stereoisomers.

Compounds

The present disclosure provides ionic liquid derivatives of pilocarpine formed from the reaction oligoethylene glycol (OEG) derivatives and pilocarpine.

In one aspect, a compound of Formula I is provided:

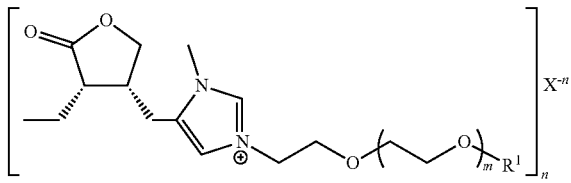

(I)

wherein:
$R^1$ is selected from hydrogen or $C_1$-$C_4$ alkyl;
m is 1, 2, 3, 4, 5, 6, 7, 8, 9, 10, 11, 12, 13, 14, 15, 16, 17, 18, 19, or 20;
$X^{-n}$ is a suitable anion having a charge of –n; and
n is 1, 2, or 3.

In some embodiments of Formula I, $R^1$ is hydrogen. In some embodiments of Formula I, $R^1$ is methyl.

In some embodiments of Formula I, m is 1. In some embodiments of Formula I, m is 2. In some embodiments of Formula I, m is 3. In some embodiments of Formula I, m is 4. In some embodiments of Formula I, m is 5. In some embodiments of Formula I, m is 6. In some embodiments of Formula I, m is 7. In some embodiments of Formula I, m is 8. In some embodiments of Formula I, m is 9. In some embodiments of Formula I, m is 10. In some embodiments of Formula I, m is 11. In some embodiments of Formula I, m is 12. In some embodiments of Formula I, m is 13. In some embodiments of Formula I, m is 14. In some embodiments of Formula I, m is 15. In some embodiments of Formula I, m is 16. In some embodiments of Formula I, m is 17. In some embodiments of Formula I, m is 18. In some embodiments of Formula I, m is 19. In some embodiments of Formula I, m is 20.

$X^{-n}$ may be selected from any pharmaceutically acceptable anion, which include anions which are acceptable for human consumption. Representative examples of anions which may be used include, but are not limited to, chloride, bromide, sulfate, hydrogen sulfate, sulfamate, phosphate, monohydrogen phosphate, dihydrogen phosphate, nitrate, acetate, propionate, succinate, glycolate, stearate, lactate, salicylate, mesylate, esylate, besylate, sulfanilate, 2-acetoxybenzoate, fumarate, toluenesulfonate, methanesulfonate, ethane disulfonate, oxalate, isethionate, malonate, glutarate, adipate, and the like.

In particular embodiments, $X^{-n}$ comprises chloride and n is 1.

In particular embodiments, the compound of Formula I is selected from:

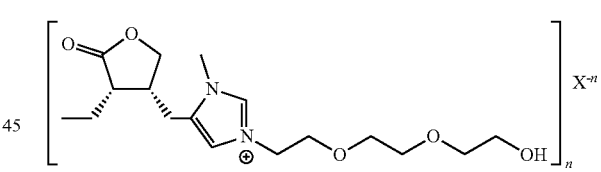

wherein $X^{-n}$ and n are as defined herein.

In particular embodiments, the compound of Formula I is

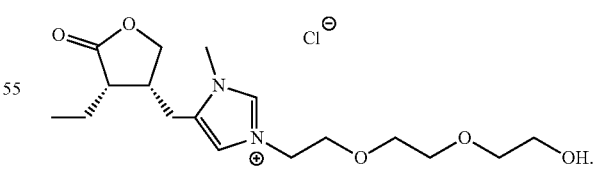

The present disclosure also includes compounds of Formula I with at least one desired isotopic substitution of an atom, at an amount above the natural abundance of the isotope, i.e., enriched.

Examples of isotopes that can be incorporated into compounds of the present disclosure include isotopes of hydrogen, carbon, nitrogen, oxygen, phosphorous, fluorine, and chlorine, such as $^2$H, $^3$H, $^{11}$C, $^{13}$C, $^{15}$N, $^{17}$O, $^{18}$O, $^{18}$F, $^{31}$P, $^{32}$P, $^{35}$S, $^{36}$Cl, and $^{125}$I, respectively. In one embodiment, isotopically labeled compounds can be used in metabolic studies (with $^{14}$C) reaction kinetic studies (with, for example $^{2}$H or $^{3}$H), detection or imaging techniques, such as positron emission tomography (PET) or single-photon emission computed tomography (SPECT) including drug and substrate tissue distribution assays, or in radioactive treatment of patients. In particular, an $^{18}$F labeled compound may be particularly desirable for PET or SPECT studies. Isotopically labeled compounds of this invention and prodrugs thereof can generally be prepared by carrying out the procedures disclosed herein by substituting a readily available isotopically labeled reagent for a non-isotopically labeled reagent.

By way of general example and without limitation, isotopes of hydrogen, for example deuterium ($^{2}$H) and tritium ($^{3}$H) may optionally be used anywhere in described structures that achieves the desired result. Alternatively or in addition, isotopes of carbon, e.g., $^{13}$C and $^{14}$C, may be used. In one embodiment, the isotopic substitution is replacing hydrogen with a deuterium at one or more locations on the molecule to improve the performance of the molecule as a drug, for example, the pharmacodynamics, pharmacokinetics, biodistribution, half-life, stability, AUC, $T_{max}$, $C_{max}$, etc. For example, the deuterium can be bound to carbon in allocation of bond breakage during metabolism (an alpha-deuterium kinetic isotope effect) or next to or near the site of bond breakage (a beta-deuterium kinetic isotope effect).

Isotopic substitutions, for example deuterium substitutions, can be partial or complete. Partial deuterium substitution means that at least one hydrogen is substituted with deuterium. In certain embodiments, the isotope is 80, 85, 90, 95, or 99% or more enriched in an isotope at any location of interest. In some embodiments, deuterium is 80, 85, 90, 95, or 99% enriched at a desired location. Unless otherwise stated, the enrichment at any point is above natural abundance, and in an embodiment is enough to alter a detectable property of the compounds as a drug in a human.

The compounds of the present disclosure may form a solvate with solvents (including water). Therefore, in one embodiment, the invention includes a solvated form of the active compound. The term "solvate" refers to a molecular complex of a compound of the present invention (including a salt thereof) with one or more solvent molecules. Non-limiting examples of solvents are water, ethanol, dimethyl sulfoxide, acetone and other common organic solvents. The term "hydrate" refers to a molecular complex comprising a disclosed compound and water. Pharmaceutically acceptable solvates in accordance with the invention include those wherein the solvent of crystallization may be isotopically substituted, e.g., $D_2O$, d6-acetone, or d6-DMSO. A solvate can be in a liquid or solid form.

Ophthalmological Compositions

The compounds of the present disclosure may be formulated as pharmaceutical compositions which are suitable for administration to the eye, i.e., ophthalmological compositions. In particular embodiments, the ophthalmological composition is of a form suitable for topical application to the eyes, for example eye drops such as aqueous ophthalmic solutions, aqueous ophthalmic suspensions, non-aqueous ophthalmic solutions and non-aqueous ophthalmic suspensions, gels, and ophthalmic ointments. Upon formulation, an ophthalmologically acceptable carrier can be used. No particular limitation is imposed on the carrier usable here insofar as it is ordinarily employed in the preparation of ophthalmic formulations.

Representative examples carriers which may be used in the disclosed topical ophthalmological compositions include, but are not limited to, inert diluents, preservatives, isotonic agents, buffers, stabilizers, pH regulators, thickeners, surfactants and ointment bases. Examples of inert diluents include, but are not limited to, aqueous solvents such as water, Ringer's solution, and isotonic saline solution, and oil solvents such as castor oil, olive oil, sesame oil, soybean oil, liquid paraffin, propylene glycol, and β-octyl-dodecanol. Examples of preservatives include, but are not limited to, parabens such a methylparaben, ethylparaben, propylparaben, and butylparaben, benzalkonium chloride, chlorhexidine, benzethonium chloride, benzyl alcohol, sorbic acid and salts thereof, thimerosal and chlorobutanol. Examples of isotonic agents include, but are not limited to, sodium chloride, mannitol, sorbitol, and glycerin. An exemplary stabilizer is ethylenediamine tetraacetate. Examples of pH regulators include, but are not limited to, hydrochloric acid, acetic acid, and sodium hydroxide. Examples of ointment bases include, but are not limited to, Vaseline, plastibase, and liquid paraffin. Examples of thickeners include, but are not limited to, methyl cellulose, carmellose and salts thereof, hydroxyethyl cellulose, sodium alginate, carboxyvinyl polymer, and polyvinylpyrrolidone. Examples of surfactants include, but are not limited to, polyethylene glycol, propylene glycol, polyoxyethylene hydrogenated castor oil, and polysorbate. For the preparation of a gel compositions, suitable excipients include, but are not limited to, carboxyvinyl polymer, methyl cellulose, sodium alginate, hydroxypropylcellulose or ethylene maleic anhydride polymer.

In some embodiments, the ophthalmological composition may further comprise one or more additional anti-glaucoma therapeutics. In some embodiments, the additional anti-glaucoma therapeutic may comprise a prostaglandin analog, a parasympthomimetic (miotic) agent (such as a cholinergic or anticholinesterase agent), a carbonic anhydrase inhibitor, an adrenergic antagonist (such as a nonselective of selective $β_1$ antagonist), an $α_2$ andrenergic agonist, or a hyperosmotic agent. Representative examples of additional anti-glaucoma therapeutics which may be used include, but are not limited to, latanoprost, bimatoprost, travoprost, tafluprost, timolol, levobunolol, betaxolol, carteolol, metipranolol, brimonidine, apraclonidine, epinephrine, echothiophate, dorzolamide, brinzolamide, methazolamide, and acetazolamide. In some embodiments, the compounds described herein may improve the solubility of the above additional anti-glaucoma therapeutics; while not wishing to be bound by any one theory, this may be the result of the ionic liquid properties of the compounds described herein.

The active ingredient may be administered in such amounts, time, and route deemed necessary in order to achieve the desired result. The exact amount of the active ingredient will vary from subject to subject, depending on the species, age, and general condition of the subject, the severity of the medical disorder, the particular active ingredient, its mode of administration, its mode of activity, and the like. The active ingredient, whether the active compound itself, or the active compound in combination with an agent, is preferably formulated in dosage unit form for ease of administration and uniformity of dosage. It will be understood, however, that the total daily usage of the active ingredient will be decided by the attending physician within the scope of sound medical judgment. The specific therapeutically effective dose level for any particular subject will depend upon a variety of factors including the disorder being treated and the severity of the disorder; the activity of the active ingredient employed; the specific composition employed; the age, body weight, general health, sex and diet of the patient; the time of administration, route of administration, and rate of excretion of the specific active ingredient employed; the duration of the treatment; drugs used in combination or coincidental with the specific active ingredient employed; and like factors well known in the medical arts.

The exact amount of an active ingredient required to achieve a therapeutically or prophylactically effective amount will vary from subject to subject, depending on species, age, and general condition of a subject, severity of the side effects or disorder, identity of the particular compound(s), mode of administration, and the like. The amount to be administered to, for example, a child or an adolescent can be determined by a medical practitioner or person skilled in the art and can be lower or the same as that administered to an adult.

Useful dosages of the active agents and pharmaceutical compositions disclosed herein can be determined by comparing their in vitro activity, and in vivo activity in animal models. Methods for the extrapolation of effective dosages in mice, and other animals, to humans are known to the art.

The dosage ranges for the administration of the compositions are those large enough to produce the desired effect in which the symptoms or disorder are affected. The dosage should not be so large as to cause adverse side effects, such as unwanted cross-reactions, anaphylactic reactions, and the like. Generally, the dosage will vary with the age, condition, sex and extent of the disease in the patient and can be determined by one of skill in the art. The dosage can be adjusted by the individual physician in the event of any counterindications. Dosage can vary, and can be administered in one or more dose administrations daily, for one or several days.

Methods of Use

The present disclosure also provides methods for the treatment of glaucoma by administering a compound or composition described herein. Thus in one aspect, a method for treating glaucoma in a subject in need thereof is provided comprising administering to the subject a therapeutically effective amount of a compound of Formula I or an ophthalmological composition as described herein. Glaucoma which may be treated as described herein includes, but is not limited to, primary glaucoma (and its variants), developmental glaucoma, or secondary glaucoma.

Glaucoma is an umbrella term for eye conditions which damage the optic nerve and can lead to a loss of vision. The main cause of damage to the optic nerve is intraocular pressure, excessive fluid pressure within the eye, which can be due to various reasons including blockage of drainage ducts and narrowing or closure of the angle between the iris and cornea. The primary categorization of types of glaucoma is between open-angle and closed-angle (or angle-closure) glaucoma. In open angle glaucoma, the iris meets the cornea normally, allowing the fluid from inside the eye to drain, thus relieving the internal pressure. Where this angle is narrowed or closed, pressure increases over time, causing damage to the optic nerve, leading to blindness.

Primary glaucoma includes primary open-angle glaucoma (also known as chronic open-angle glaucoma, chronic simple glaucoma, or glaucoma simplex) such as high-tension glaucoma or low-tension glaucoma, primary angle closure glaucoma (also known as primary closed-angle glaucoma, narrow-angle glaucoma, pupil-block glaucoma, or acute congestive glaucoma) such as acute angle closure glaucoma, chronic angle closure glaucoma, intermittent angle closure glaucoma, or superimposed on chronic open-angle closure glaucoma. Variants of primary glaucoma include pigmentary glaucoma, exfoliation glaucoma (also known as pseudoexfoliative glaucoma or glaucoma capsulare), and primary juvenile glaucoma.

Primary angle closure glaucoma is caused by contact between the iris and the trabecular meshwork, which in turn obstructs outflow of the aqueous humor from the eye. This contact between the iris and trabecular meshwork may gradually damage the function of the meshwork until it fails to keep pace with aqueous production, leading to rising pressure. Prolonged contact between the iris and trabecular meshwork may cause the formation of synechiae, which cause permanent obstruction of aqueous outflow. In some cases, pressure may rapidly build up in the eye, causing pain and redness (i.e., acute angle closure glaucoma). In this situation, the vision may become blurred, and halos may be seen around bright lights. Accompanying symptoms may include a headache and vomiting.

In narrow angle glaucoma (also known as closed-angle glaucoma) the iris bows forward, narrowing the angle that drains the eye, increasing pressure within the eye. If untreated, it can lead to the medical emergency of angle-closure glaucoma. In angle-closure glaucoma (also known as closed-angle glaucoma, primary angle-closure glaucoma, and acute glaucoma), the iris bows forward and causes physical contact between the iris and trabecular meshwork, which blocks the outflow of aqueous humor from within the eye. This contact may gradually damage the draining function of the meshwork until it fails to keep pace with aqueous production, and the intraocular pressure rises. The onset of symptoms is sudden and causes pain and other symptoms that are noticeable; it is treated as a medical emergency. Unlike open-angle glaucoma, angle-closure glaucoma is a result of the angle between the iris and cornea closing. This tends to occur in the far-sighted, who have smaller-than-normal anterior chambers, making physical contact between the iris and trabecular meshwork more likely.

Normal-tension glaucoma (also known as low-tension glaucoma or normal-pressure glaucoma) is a condition where the optic nerve is damaged although intraocular pressure is in the normal range (12 to 22 mmHg or 1.6 to 2.9 kPa). The cause of normal-tension glaucoma is unknown, although individuals with a family history of the condition, those of Japanese ancestry, those with a history of systemic heart disease, and those with Flammer syndrome are at a higher than average risk of developing the condition.

Primary open-angle glaucoma (also known as primary glaucoma or chronic glaucoma) refers to slow clogging of the drainage canals resulting in increased eye pressure leading to progressive optic nerve damage. This manifests as gradual loss of the visual field, starting with loss of peripheral vision, but eventually all vision will be lost if not treated. Onset is slow and painless, and loss of vision is gradual. Primary open-angle glaucoma is when damage to the optic nerve results in progressive loss of the visual field and is associated with increased pressure in the eye. Not all patients with primary open-angle glaucoma have eye pressure that is elevated above normal, but decreasing the eye pressure further has been shown to stop progression in this cases. The increased pressure is caused by trabecular meshwork blockage. Because the microscopic passageways are blocked, the pressure builds up in the eye and causes very gradual vision loss. Peripheral vision is affected first, but eventually the entire vision field will be lost if not treated.

Pseudoexfoliation glaucoma (also known as exfoliation glaucoma) is a condition resulting from the accumulation of microscopic granular protein fibers which can block normal drainage of the aqueous humor. Pseudoexfoliation glaucoma is prevalent in Scandinavia, primarily in those over 70 and in women.

Pigmentary glaucoma (also known as pigmentary dispersion syndrome) is caused by pigment cells sloughing off from the back of the iris and floating around the aqueous humor. These pigment cells accumulate over time in the anterior chamber in such a way that they begin to clog the trabecular meshwork.

Developmental glaucoma includes, but is not limited to, primary congenital glaucoma, infantile glaucoma, and glaucoma associated with hereditary or familial diseases.

Primary juvenile glaucoma is a neonate or juvenile abnormality where ocular hypertension is evident at birth or shortly thereafter and is caused by abnormalities in the anterior chamber angle development that blocks the outflow of the aqueous humor.

Secondary glaucoma refers to any case in which another disease, trauma, drug or procedure causes increased eye pressure, resulting in optic nerve damage and vision loss, and may be mild or severe. It can be due to an eye injury, inflammation, a tumor, or advanced cases or cataracts or diabetes. It can also be certain drugs such as steroids. Treatment will vary depending on whether it is open-angle or angle-closure glaucoma. Secondary glaucoma includes, but is not limited to, inflammatory glaucoma (such as uveitis and Fuchs heterochromic iridocyclitis), phacogenic glaucoma (such as angle-closure glaucoma with mature cataract, phacoanalphylactic glaucoma secondary to rupture of lens capsule, phacolytic glaucoma due to phacotoxic meshwork blockage, and subluxation of lens), glaucoma secondary to intraocular hemorrhage (such as hyphema and hemolytic glaucoma), traumatic glaucoma (such as angle recession glaucoma, postsurgical glaucoma, aphakic pupillary block, and ciliary block glaucoma), neovascular glaucoma, drug-induced glaucoma (such as corticosteroid induced glaucoma and alpha-chymotrypsin glaucoma), and glaucoma of miscellaneous origin (such as associated with intraocular tumors, retinal detachments, or essential iris atrophy, secondary to severe chemical burns of the eye, or toxic glaucoma).

Neovascular glaucoma, an uncommon type of glaucoma, is difficult to treat and is often caused by proliferative diabetic neuropathy or central retinal vein occlusion. It may also be triggered by other conditions that result in ischemia of the retina or ciliary body. Individuals with poor blood flow to the eye are highly at risk for this condition. Neovascular glaucoma results when new, abnormal vessels begin developing in the angle of the eye that blocks drainage. Patients with this condition rapidly lose their eyesight, sometimes appearing very rapidly after cataract surgery procedures.

Uveitis glaucoma is due to uveitis, the swelling and inflammation of the uvea, the middle layer of the eye. Increased eye pressure in uveitis can result from the inflammation itself or from the steroids used to treat it.

Toxic glaucoma is open-angle glaucoma with an unexplained significant rise of intraocular pressure following unknown pathogenesis. It characteristically manifests as ciliary body inflammation and massive trabecular edema that sometimes extends to Schlemm's canal. This condition is differentiated from malignant glaucoma by the presence of a deep and clear anterior chamber, a lack of aqueous misdirection, and where the corneal appearance is not as hazy. A reduction in visual acuity can occur following neuroretinal breakdown. Associated factors include inflammation, drugs, trauma, and intraocular surgery, including cataract surgery and vitrectomy procedures.

In some embodiments, the compounds or compositions described herein may be administered in combination or alternation with one or more additional therapeutic agents. In some embodiments, the additional therapeutic agent may comprise an anti-glaucoma therapeutic. In some embodiments, the additional anti-glaucoma therapeutic may comprise a prostaglandin analog, a parasympthomimetic (miotic) agent (such as a cholinergic or anticholinesterase agent), a carbonic anhydrase inhibitor, an adrenergic antagonist (such as a nonselective of selective $\beta_1$ antagonist), an $\alpha_2$ andrenergic agonist, or a hyperosmotic agent. Representative examples of additional anti-glaucoma therapeutics which may be used include, but are not limited to, latanoprost, bimatoprost, travoprost, tafluprost, timolol, levobunolol, betaxolol, carteolol, metipranolol, brimonidine, apraclonidine, epinephrine, echothiophate, dorzolamide, brinzolamide, methazolamide, and acetazolamide.

A number of embodiments of the disclosure have been described. Nevertheless, it will be understood that various modifications may be made without departing from the spirit and scope of the invention. Accordingly, other embodiments are within the scope of the following claims.

By way of non-limiting illustration, examples of certain embodiments of the present disclosure are given below.

EXAMPLES

The following examples are put forth so as to provide those of ordinary skill in the art with a complete disclosure and description of how the compounds, compositions, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in degrees Celsius or is at ambient temperature, and pressure is at or near atmospheric pressure.

Ionic Liquid Pilocarpine Analog as an Antiglaucoma Drug

A representative ionic liquid pilocarpine analog, [Pilo-OEG]Cl, a first-of-its-kind ionic liquid antiglaucoma drug, is synthesized and characterized in this example. Pilocarpine was reacted with the oligo-polyethylene glycol chloride, 2-[2-(2-chloroethoxy) ethoxy] ethanol, to form an ionic liquid molecule with an imidazole cation and a chloride anion. The chemical structure of [Pilo-OEG]Cl was identified by $^1$H NMR spectroscopy. Compared with pilocarpine (Pilo) and pilocarpine hydrochloride (PiloHCl), [Pilo-OEG]Cl gained improved structural stability according to pH measurements and LC-MS analysis. The permeability coefficient of [Pilo-OEG]Cl is 1-fold higher than Pilo and 8-fold higher than PiloHCl. [Pilo-OEG]Cl did not show apparent toxicity to human corneal epithelial cells over a broad range of concentrations up to 50 mM. According to in vivo efficacy assessment of PiloHCl and [Pilo-OEG]Cl in normotensive adult Brown Norway female rats, [Pilo-OEG]Cl was 2-fold more potent than PiloHCl in reducing intraocular pressure (IOP) reduction. Taken together, [Pilo-OEG]Cl has enhanced stability, cytocompatibility, corneal permeability, and better IOP lowering efficacy, thus making a promising new drug candidate for antiglaucoma therapy. Transforming old antiglaucoma drugs to pharmaceutically active ionic liquids represents an innovative approach to develop improved glaucoma medications.

Introduction

Drugs may have issues such as unpredictable polymorphic conversion, poor water solubility, low bioavailability, collectively limiting their therapeutic benefits.[1] Converting active pharmaceutical ingredient (API) to salts has proven to be effective in improving their physicochemical properties such as solubility without compromising therapeutic activities.[1-5] An estimated 50% of APIs are produced in the salt form.[6] Recently liquid salts have attracted increasing consideration for their potential use in drug development and improvement. Ionic liquids (ILs) are a class of ionic, salt-like substances that appear in the liquid form at low temperatures.[7,8] Owing to their unique physical and chemical features, ILs have been broadly studied as solvents, energetic materials, catalysts, and so on.[9] The application of ILs as pharmaceuticals has also explored.[6,10-16] Davis et al. reported the first IL drug derived from the antifungal drug miconazole.[17] This new IL drug was made through the reaction between imidazole-ring and alkyl iodides, followed by an anion metathesis. Not only do IL drugs have improved water solubility[11] but also they become thermodynamically stable, hence avoiding polymorphic conversion issue. IL drugs possess both therapeutic activities and the features of ionic liquids. Such appealing dual functionality suggests a new strategy for effective formulation of old drugs.[18]

Pilocarpine is a cholinergic drug that has been used as glaucoma medication for many years.[19] Pilocarpine induces miosis to facilitate aqueous humor outflow, thus reducing intraocular pressure (IOP) to mitigate vision loss.[20,21] The commonly used APIs in pilocarpine eye drops are pilocarpine hydrochloride or pilocarpine nitrate, both in salt form (FIG. 1A). In this work, we report the synthesis and characterization of an IL-like pilocarpine analog, [Pilo-OEG]Cl, the first-of-its-kind ionic liquid antiglaucoma drug. We assessed its cytocompatibility, corneal permeability and its IOP-lowering effect.

Experimental

Materials. Pilocarpine (Pilo), pilocarpine hydrochloride (PiloHCl), 2-[2-(2-chloroethoxy) ethoxy] ethanol, triethylamine (TEA), and WST-1 assay were purchased from Sigma Aldrich. Phosphate Buffered Saline (PBS, 10×) was purchased from Fisher and diluted to 1× before use.

Synthesis of ionic liquid pilocarpine analog ([Pilo-OEG] Cl). Pilo (0.5 mmol, 104 mg) was mixed with 2-[2-(2-chloroethoxy) ethoxy] ethanol (0.53 mmol, 92 mg), and the mixture was heated to 120° C. to allow reflux. $^1$H NMR (Bruker 600 MHz spectrometer) spectroscopy was used to monitor reaction progress. The reaction was not stopped until the proton peaks at 6.75 and 7.57 ppm disappeared. [Pilo-OEG]Cl was obtained without further purification. $^1$H NMR (600 MHz, D$_2$O) δ 8.63 (s, 1H), 7.32 (s, 1H), 4.26 (dt, J=20.1, 4.3 Hz, 4H), 4.05 (dd, J=9.6, 3.2 Hz, 1H), 3.85-3.42 (m, 13H), 2.99 (t, J=5.4 Hz, 1H), 2.80 (td, J=15.9, 5.8 Hz, 2H), 2.56 (dd, J=16.2, 11.3 Hz, 1H), 1.69 (s, 1H), 1.48 (dd, J=8.1, 6.2 Hz, 1H), 0.93 (s, 3H).

Stability test. Fresh water solutions of Pilo, PiloHCl, and [Pilo-OEG]Cl (5 mM) were prepared and their pH at 0, 0.75, 4, 8, and 24 h was measured with a pH meter (PHS-3E, INESA). The samples at 0 and 24 h were further analyzed with LC-MS/MS using a Surveyor Plus HPLC System and triple stage quadrupole (TSQ) Quantum Ultra Mass Spectrometer (Thermo Fisher Scientific, USA) equipped with an auto-sampler and electrospray ionization (ESI) source. Separation was carried out on an Hypersil Gold column (150 mm×2.1 mm, 5 m, Thermo) maintained at 25° C. The mobile phase consisted of 0.1% (v/v) formic acid water phase (A) and methanol phase (B). The gradient elution program was as follows: 95% of A at 0-5 min, and back to 95% of A at 23.1 min, re-conditioning of the column for 8 min. The flow rate was 0.2 mL/min A capillary temperature of 350° C., spray voltage of 4500 V, sheath gas of 30 arb, and auxiliary gas of 10 arb were maintained as the optimal instrument conditions. Unit resolution was used for Q1 (FWHM 0.7). Nitrogen was used as both sheath gas and auxiliary gas.

Cytotoxicity assessment. HCE-2 human corneal epithelial cells were seeded in a 96-well plate at a density of 1×10$^4$ cell/well. After attachment, the cells were incubated with various concentrations of Pilo, PiloHCl and [Pilo-OEG]Cl for 24 h and cell viability was determined by using WST-1 assay. The medium for HCE-2 (ATCC CRL-11135, epithelial Adenovirus 12-SV40 hybrid transformed) was Keratinocyte-serum free medium supplemented with 0.05 mg/mL of bovine pituitary extract (BPE), 5 ng/mL of epidermal growth factor (EGF), 500 ng/mL of hydrocortisone and 0.005 mg/mL of insulin. The cytotoxicity of Pilo and [Pilo-OEG] Cl to NIH3T3 fibroblast cells was also tested.

Ex vivo corneal permeation studies. Corneas were extracted from fresh rabbit eyes and mounted immediately in a Franz diffusion cell system with the epithelial surface facing the donor chamber. In each test, Pilo, PiloHCl, or [Pilo-OEG]Cl (200 µL, 27 mM) was loaded to the donor chamber. The receiver chamber was filled with 5 mL of PBS. At pre-determined time points up to 4 h, an aliquot of 1 mL from the receiver chamber was collected via syringe and analyzed with UV-Vis spectrophotometer (U-3010, Hitachi). Fresh PBS (1 mL) was added to the receiver chamber following each sampling. All the experiments were conducted in triplicate. The permeability coefficient, P, was then determined based on the following equation:

$$P = \frac{dQ/dt}{AC}$$

where dQ/dt is the steady-state slope of a cumulative flux curve (in this study, the data in 1 h is selected for dQ/dt calculation), C is drug concentration in the donor chamber, and A is the effective cross-sectional area (0.629 cm$^2$) available for diffusion.[22]

In vivo efficacy assessment. Normotensive adult Brown Norway female rats (Charles River Laboratories), 8 months old, were used in this work. The rats were given free access to food and water, 12 hours light and dark cycle in a temperature-controlled room (18-24° C.). The procedures conducted were approval by Virginia Commonwealth University IACUC. Rats were randomly grouped to two groups of four (n=4). The right eye of each rat was instilled with PiloHCl or [Pilo-OEG]Cl PBS solution (2×5 µL, 82 mM pilocarpine equivalent), one dose at 8:00 am and the second dose at 12:00 pm. The IOPs of both eyes were measured at 8:00 am (before dosing), 8:45 am, 12:00 pm (before the second dosing), 12:45 pm, and 16:00 pm using Icare TONO-LAB tonometer TV02.

Results and Discussion

Figure 1B:
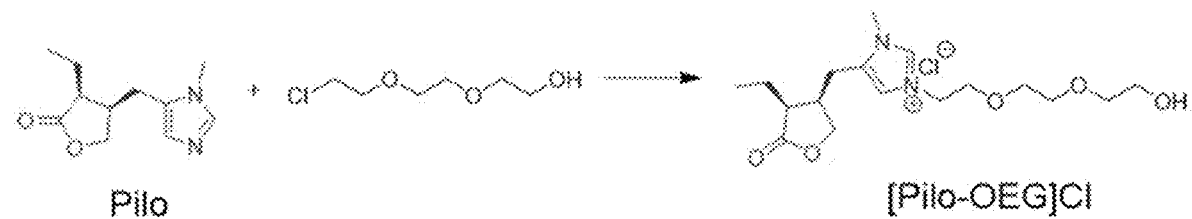
FIG. 1B shows the synthetic route for the synthesis of the exemplary ionic liquid pilocarpine analog [Pilo-OEG]Cl.
Figure 1C:
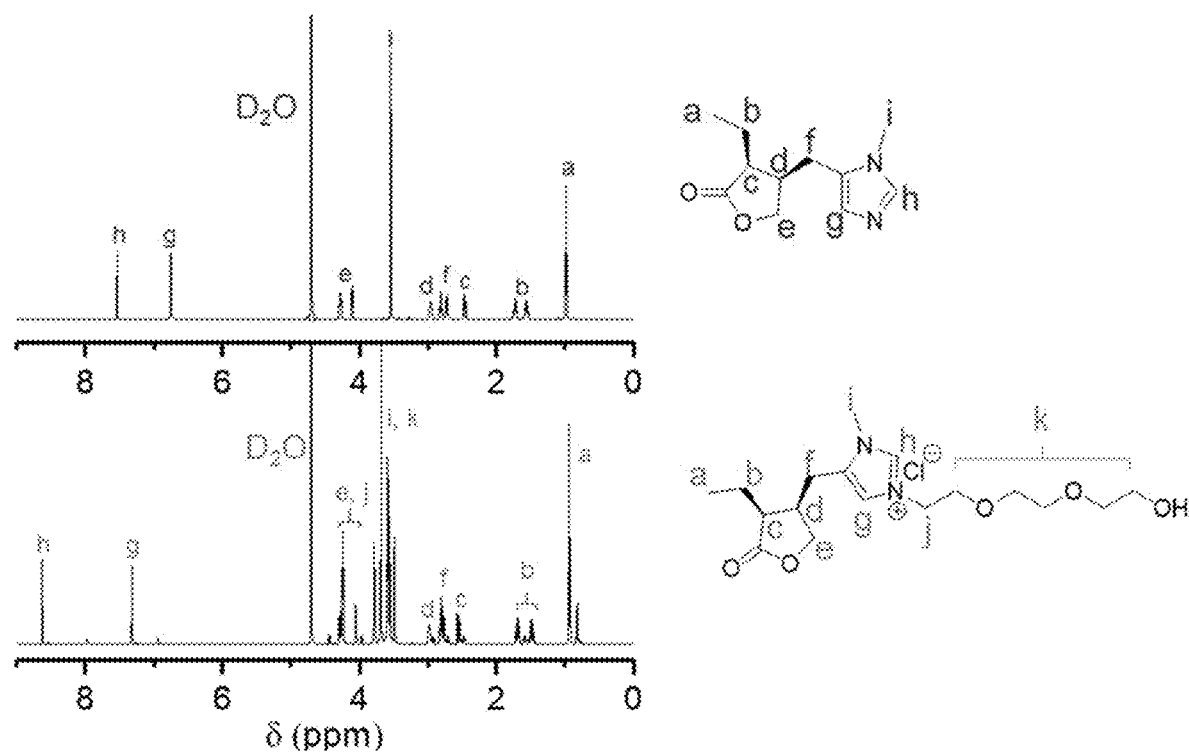
FIG. 1C shows the $^1$H NMR spectra of pilocarpine and [Pilo-OEG]Cl in $D_2O$.

IL-like pilocarpine analogue, [Pilo-OEG]Cl, resulted from the reaction between the imidazole-ring of pilocarpine with the oligo-polyethylene glycol chloride (FIG. 1b). By comparing the $^1$H NMR spectrum of Pilo (FIG. 1c), the chemical shifts of the protons in the imidazole ring (g and h) of [Pilo-OEG]Cl shifted from 6.75 and 7.57 ppm to 7.32 and 8.63 ppm. These shifts, as well as the appearance of proton peaks of OEG at 3.85-3.42 ppm, verified the successful synthesis of [Pilo-OEG]Cl.

Figure 2A:
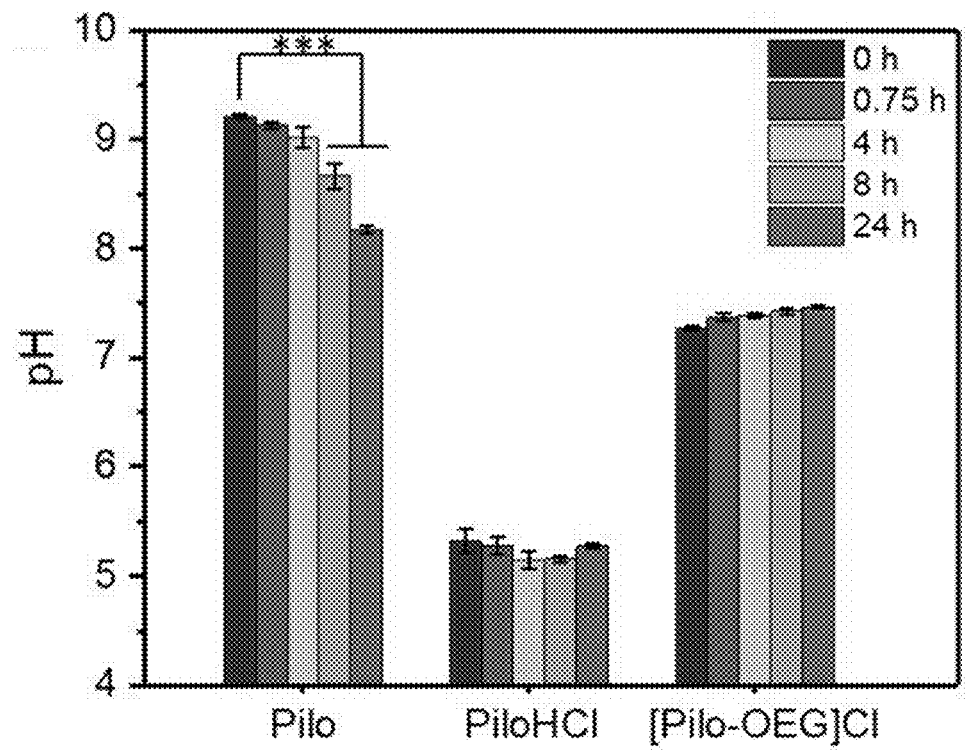
FIG. 2A shows the pH changes of pilocarpine, pilocarpine hydrochloride, and [Pilo-OEG]Cl aqueous solutions (5 mM) over a course of 24 hours. *** indicates p<0.01.
Figure 2B:
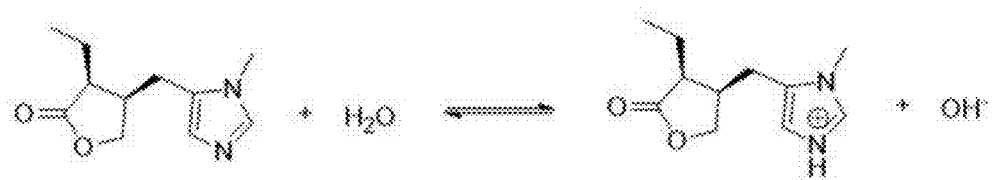
FIG. 2B shows the dissociation of pilocarpine in water.
Figure 2C:
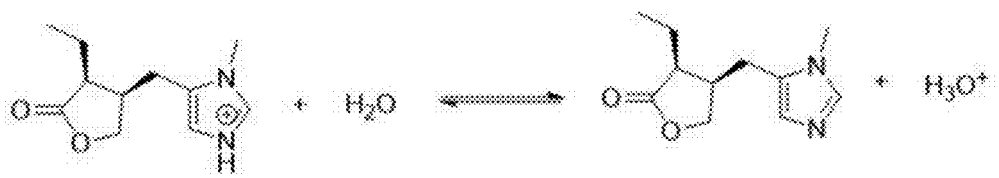
FIG. 2C shows the hydrolyzation of pilocarpine hydrochloride in water.
Figure 2D:
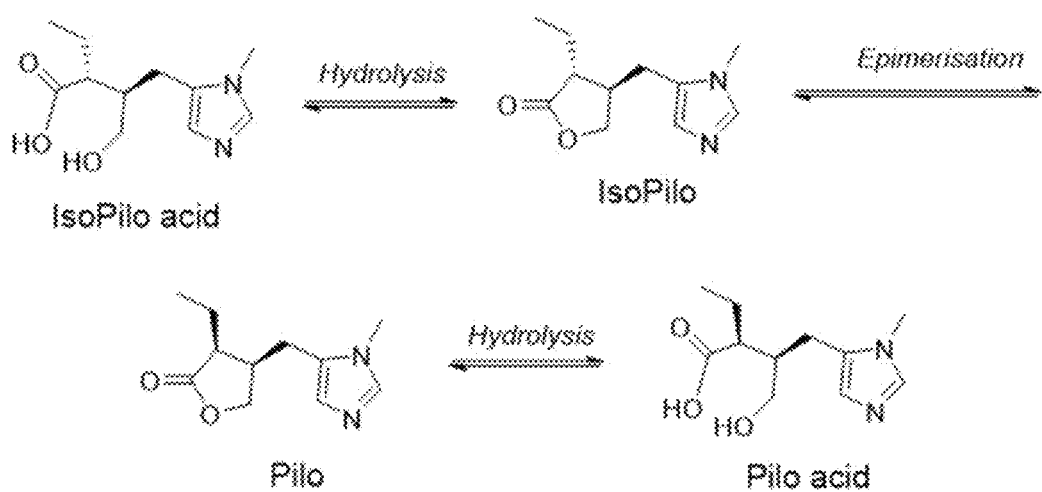
FIG. 2D shows the degradation pathways of pilocarpine.

The pH values of freshly prepared Pilo, PiloHCl, and [Pilo-OEG]Cl solutions are 9.2, 5.3, and 7.3, respectively (FIG. 2A) at the same concentration of 5 mM. Pilo is a weak alkaline drug. The dissociation of Pilo in water is shown in FIG. 2B. The dissociation constant (pKa) of Pilo was calculated to be 7.28 based on its pH at 0 h, which is consistent with the value reported in the Merck Index (7.15). As a strong acidic-weak alkaline salt, the hydrolyzation of PiloHCl in water is shown in FIG. 2C. According to our estimation, the pKa of PiloHCl is 8.34. [Pilo-OEG]Cl is an ionic liquid, and it does not alter the pH of water upon addition, a noticeable property of ionic liquids.[23] We monitored the pH values of their solutions as a means to check their structural stability. Within 24 h, the pH values of PiloHCl and [Pilo-OEG]Cl aqueous solutions remain relatively stable. However, the pH of Pilo solution drops to 8.7 at 8 h and 8.2 at 24 h, significantly deviating from its initial pH value of 9.2. Pilo in aqueous solution may hydrolyze to pilocarpine acid (Pilo acid) and/or epimerize to isopilocarpine (IsoPilo), which eventually hydrolyzes to isopilocarpine acid (IsoPilo acid) (FIG. 2D).[24] The hydrolysis of both Pilo and IsoPilo leads to lactone ring opening and the appearance of carboxyl group. Acting as a proton donor, the carboxyl group contributes to the pH decrease of the solution. Neither PiloHCl solution nor [Pilo-OEG]Cl solution experienced pH reduction, indicating their structural stability.

Figure 3A:
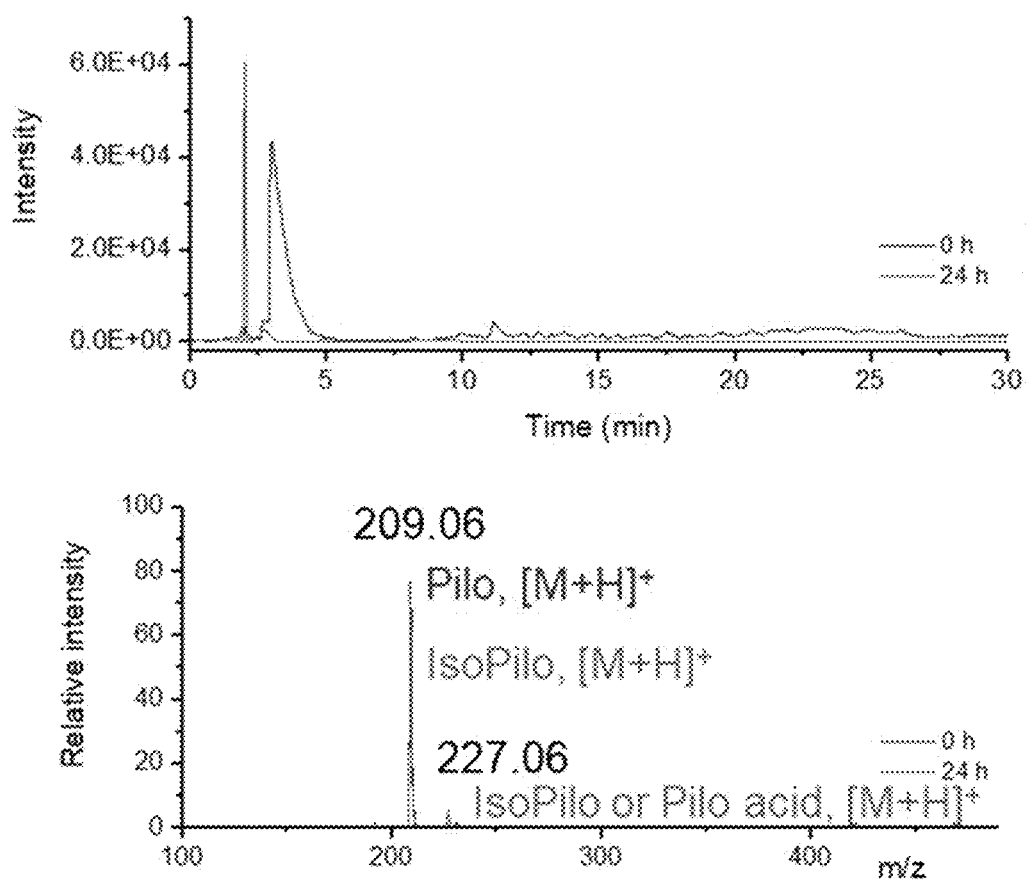
FIGS. 3A-3C show the LC-MS chromatograms of pilocarpine (FIG. 3A), pilocarpine hydrochloride (FIG. 3B), and [Pilo-OEG]Cl (FIG. 3C). In each figure, the left panel shows the LC chromatogram and the right panel shows the MS spectra of the eluents.
Figure 3B:
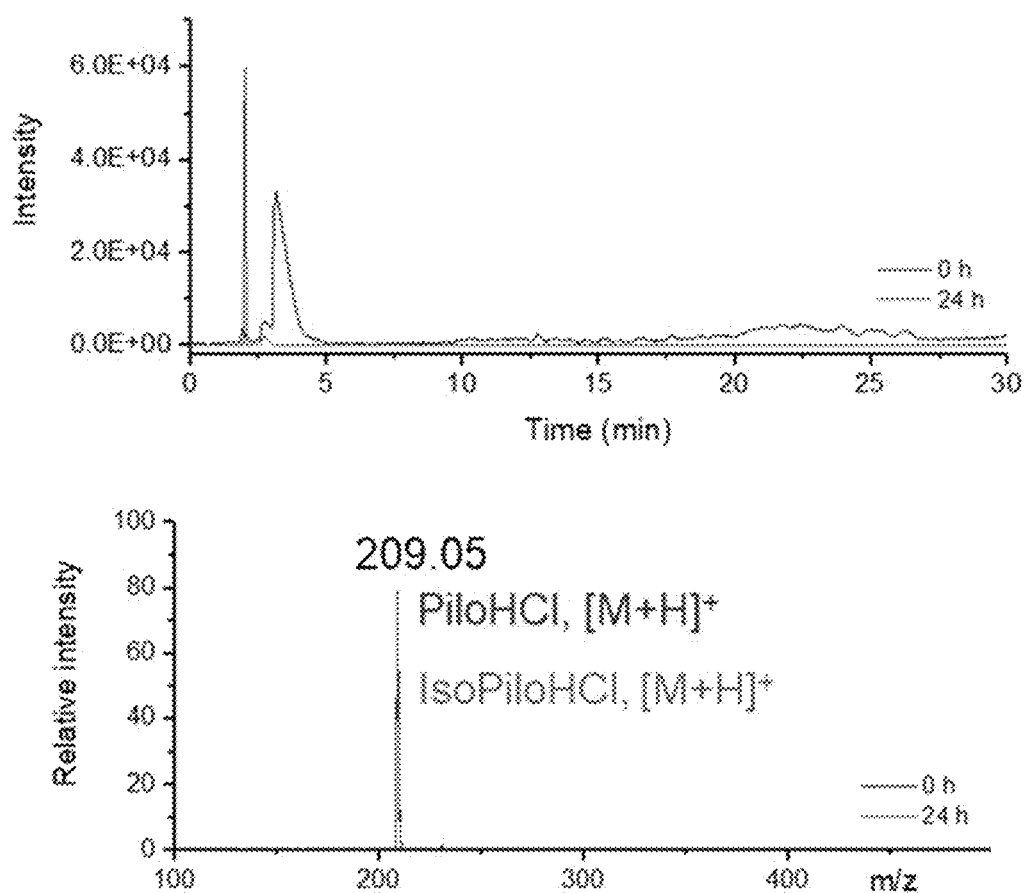
Figure 3C:
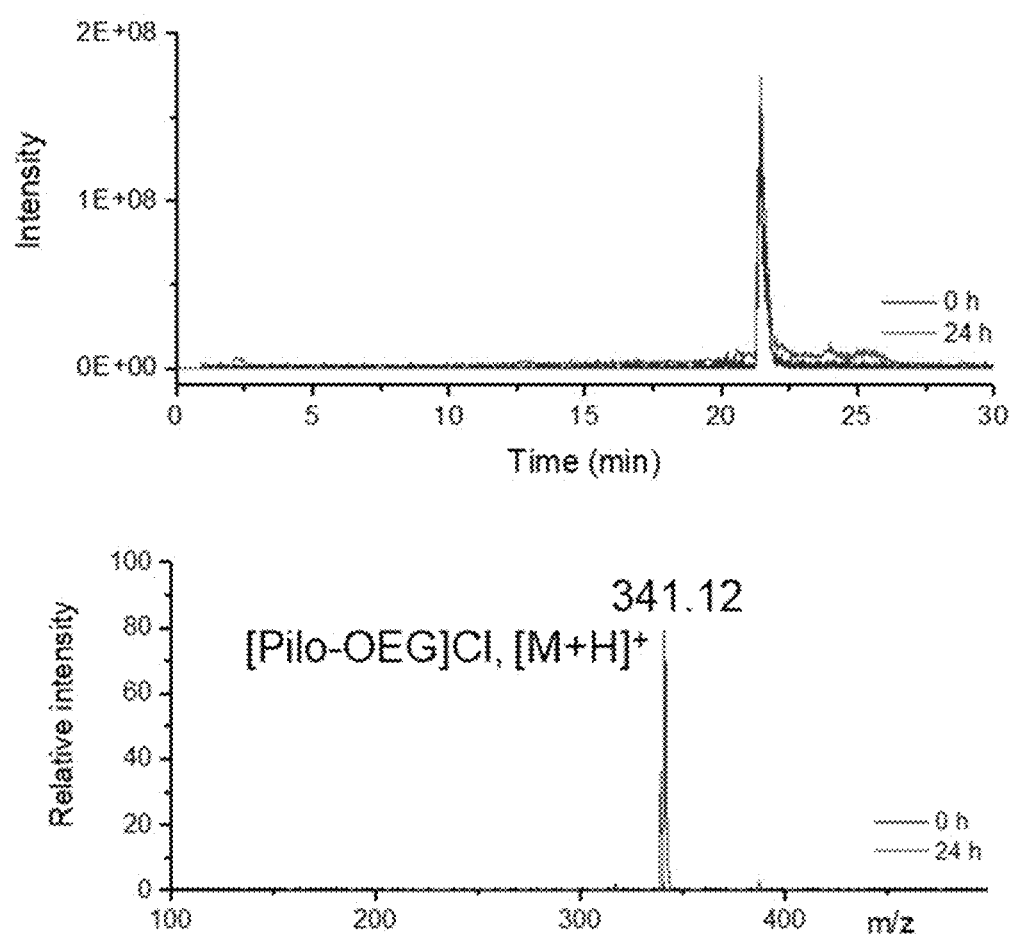

Our LC-MS analysis further ascertains the structural instability of Pilo and PiloHCl. In the Pilo solution, isopilocarpine formed (eluted at 2.02 min, m/z=209.06) and further hydrolyzed into acids (m/z=227.06) (FIG. 3A). Isopilocarpine also formed in the PiloHCl solution although no hydrolyzed pilocarpine or isopilocarpine (acids) was detected (FIG. 3B). In contrast, neither isopilocarpine or pilocarpine and isopilocarpine acids formed in the [Pilo-OEG]Cl solution (FIG. 3C). Since isopilocarpine, pilocarpine acid, and isopilocarpine acid are pharmacologically inactive, the superior stability of [Pilo-OEG]Cl compared with Pilo and PiloHCl becomes a huge advantage.

Figure 4:
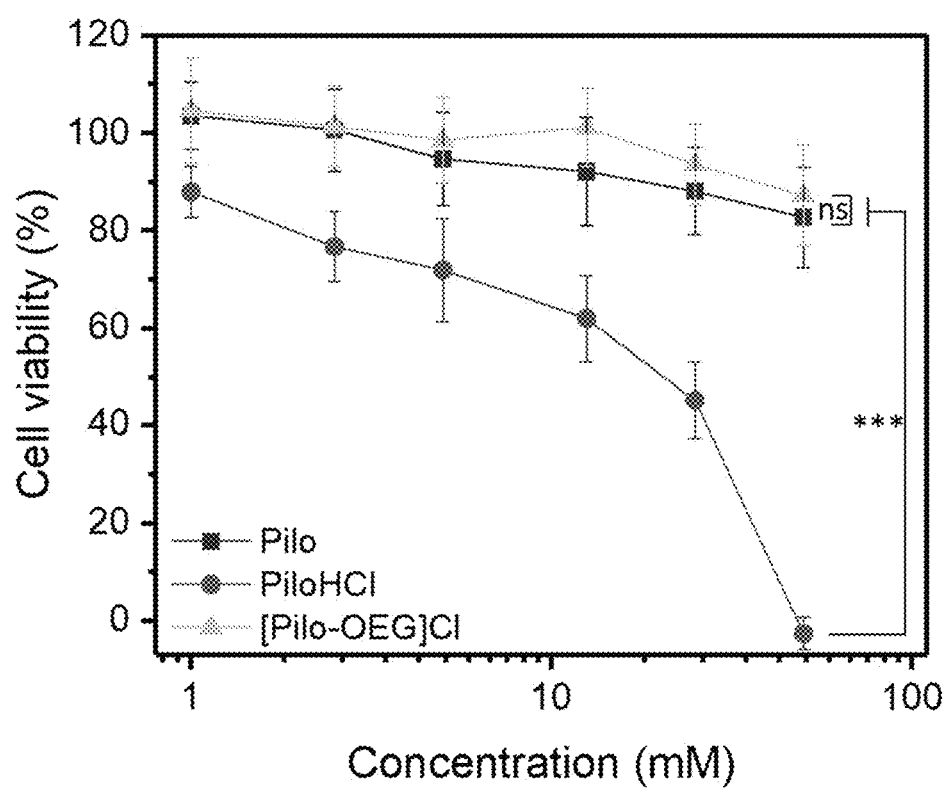
FIG. 4 shows the cytotoxicity of pilocarpine, pilocarpine hydrochloride, and [Pilo-OEG]Cl on HCE-2 cells. *** represented P<0.001.
Figure 7:
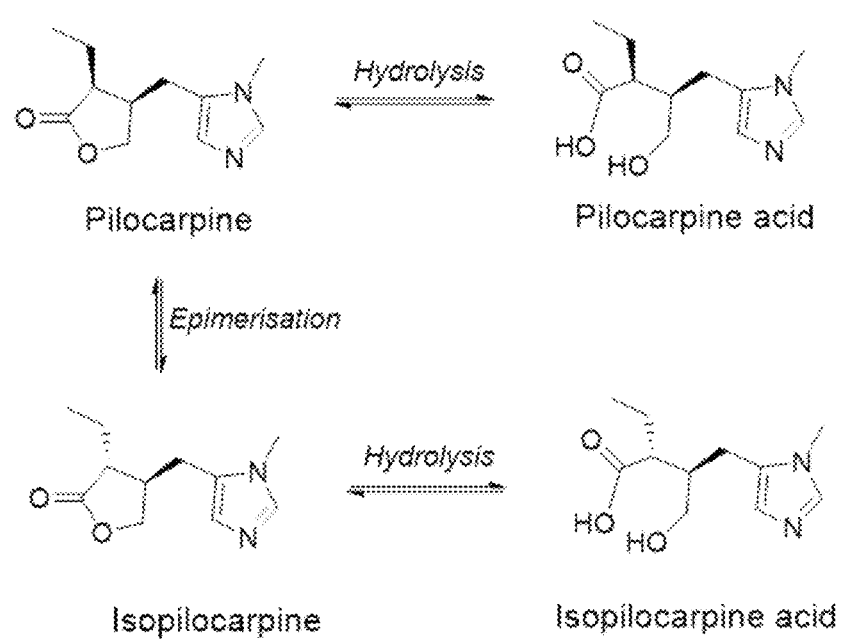
FIG. 7 shows the degradation pathways of pilocarpine.
Figure 8:
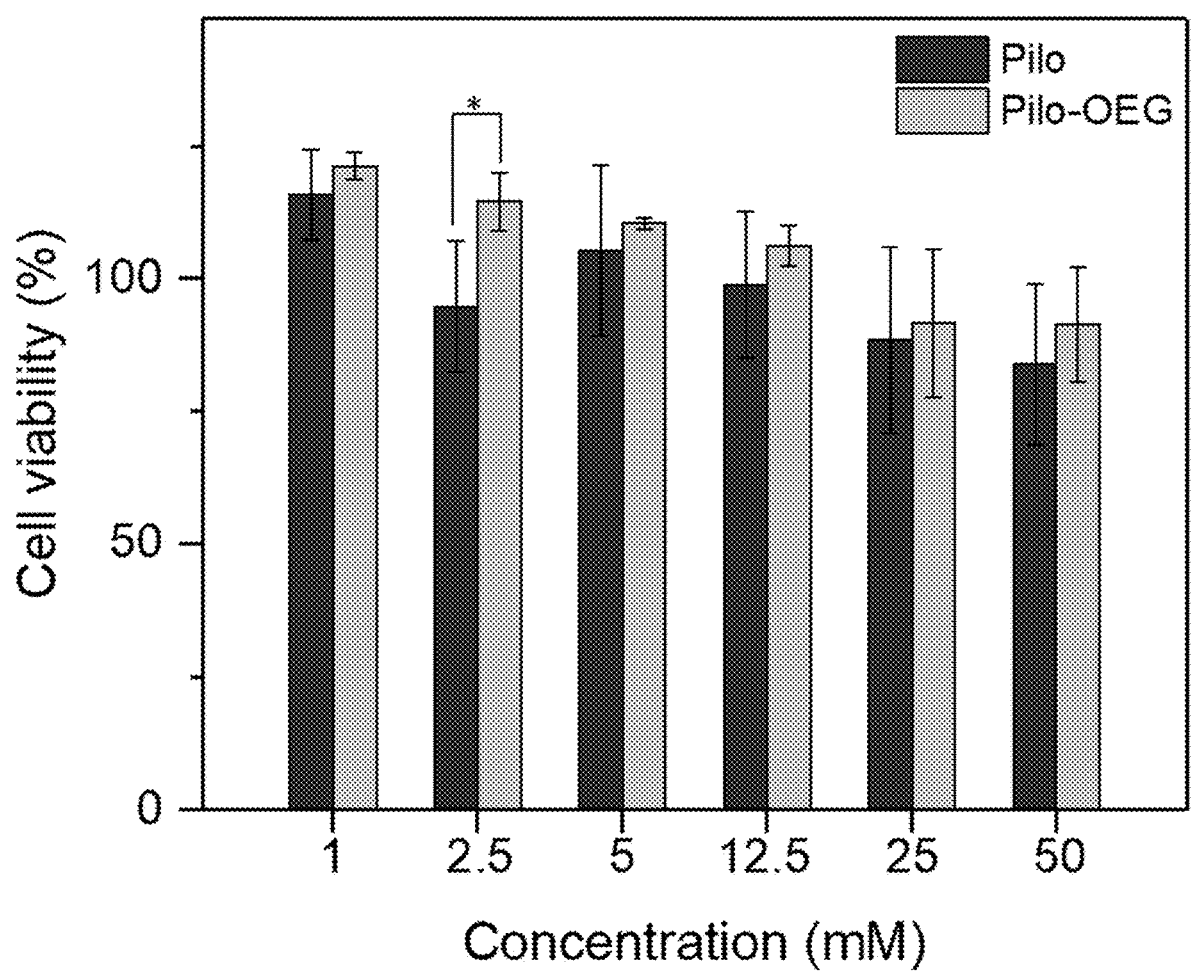
FIG. 8 shows the cytotoxicity of pilocarpine and [Pilo-OEG]Cl to NIH3T3 cells. * indicates p<0.05.

The cytotoxicity of ILs has been a debate topic delaying their entry into biological field. In this study, we examined the cytotoxicity of the newly formed [Pilo-OEG]Cl to both NIH3T3 fibroblast cells (FIG. 7) and HCE-2 human cornea epithelium cells (FIG. 4). PiloHCl shows strong dose-dependent cytotoxicity. Its IC50 was determined to be 25 mM. Within a wide range of concentrations (1 mM to 50 mM), both Pilo and [Pilo-OEG]Cl are cytocompatible.

Figure 5:
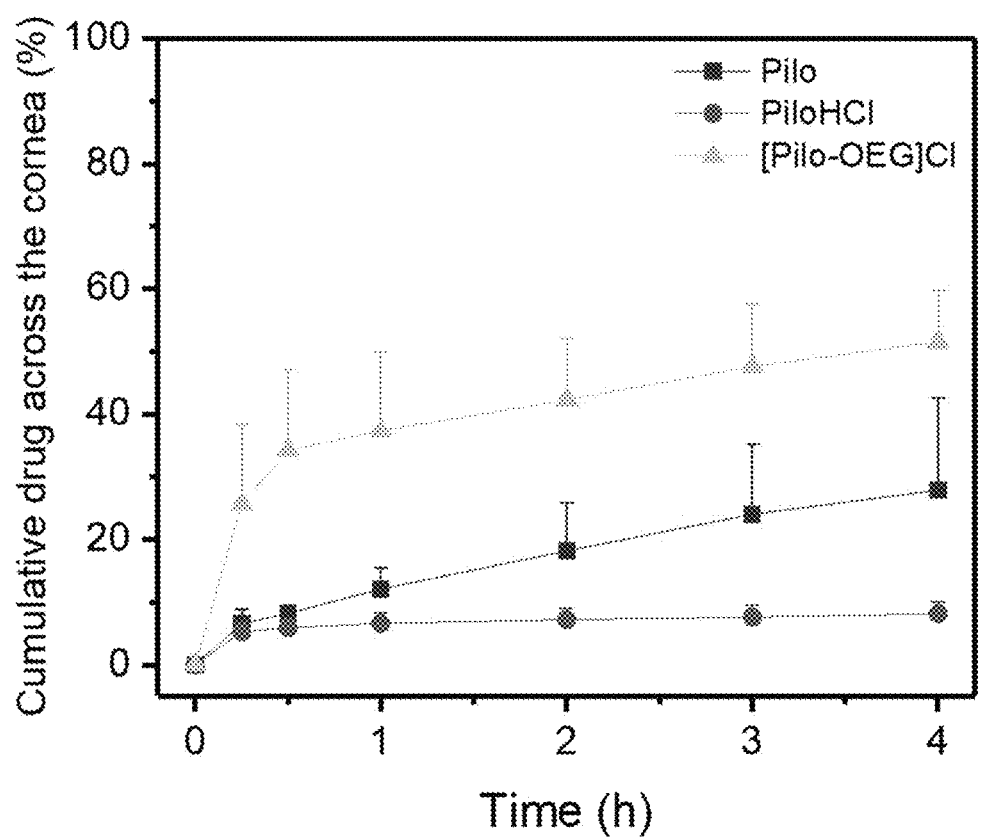
FIG. 5 shows the permeability of pilocarpine, pilocarpine hydrochloride, and [Pilo-OEG]Cl across the cornea.

We studied the permeation behavior of Pilo, PiloHCl, and [Pilo-OEG]Cl across the rabbit cornea. As shown in FIG. 5, within 4 h, 27.8±14.7% of Pilo, 8.1±1.8% of PiloHCl permeated through the cornea, respectively, while as high as 51.6±8.1% of [Pilo-OEG]Cl (5-fold higher than PiloHCl) crossed the cornea. The permeability coefficient of [Pilo-OEG]Cl was calculated to be $1.3 \times 10^{-5}$ cm/s, while the permeability coefficients of Pilo and PiloHCl are $6.6 \times 10^{-6}$ cm/s and $1.5 \times 10^{-6}$ cm/s, respectively. The permeability coefficient of [Pilo-OEG]Cl is 1-fold higher than Pilo and 8-fold higher than PiloHCl.

Figure 6:
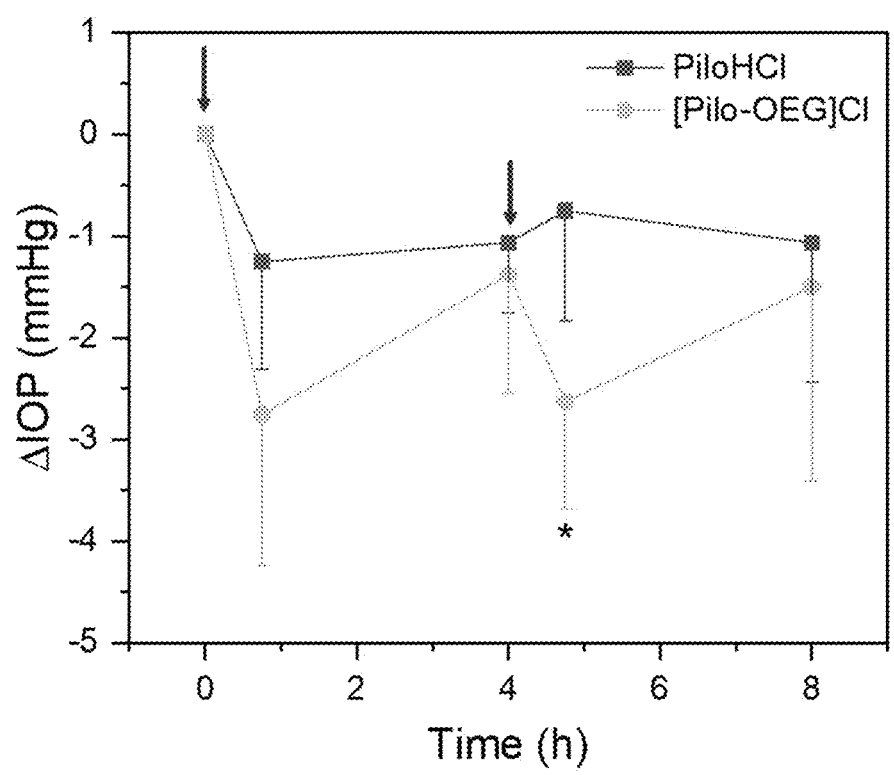
FIG. 6 shows the in vivo IOP-lowering effects of pilocarpine hydrochloride and [Pilo-OEG]Cl in normotensive rats following two-time topical instillation. Arrows mean instillation. n=4; *P<0.05, pilocarpine hydrochloride versus [Pilo-OEG]Cl.

While the improved in vitro and transport properties of [Pilo-OEG]Cl is encouraging, it is also critical for [Pilo-OEG]Cl to show IOP lowing effects. We examined the in vivo IOP lowing effects of [Pilo-OEG]Cl in normotensive adult Brown Norway female rats. PiloHCl was included as a positive control. Similar to PiloHCl (FIG. 6), the highest IOP reduction is seen at 45 min post-administration. Although statistical significance was not established, [Pilo-OEG]Cl lowers the IOP by an average of 2.75 mmHg, 2-fold higher than the IOP reduction by the PiloHCl (1.25 mmHg). A second dose was applied 4 hours after the first dose. The second dose of PiloHCl kept IOP reduction of ~1 mmHg. In contrast, a second dose of [Pilo-OEG]Cl induced a deeper IOP reduction of 2.625 mmHg Overall, [Pilo-OEG]Cl was shown to be more effective than PiloHCl.

Conclusion

In conclusion, we synthesized an ionic liquid pilocarpine analog, [Pilo-OEG]Cl. Compared to PiloHCl, [Pilo-OEG]Cl shows enhanced stability, cytocompatibility, corneal permeability, and in vivo IOP lowing efficacy. This work represents a new way to develop effective formulations for old glaucoma drugs. [Pilo-OEG]Cl exhibits enhanced stability in aqueous media, cytocompatibility, and cornea permeability without compromising water solubility. Besides the improved physical and biological properties owning to its unique IL form, this new antiglaucoma drug, [Pilo-OEG]Cl, could be further tailored to have additional features. The chloride anion could be altered by anion metathesis readily. The moiety oligo-PEG could be substituted with other chloride-containing compounds or drugs. The incorporation of the OEG moiety endows [Pilo-OEG]Cl with possibility for further chemical modification via its hydroxyl end-group.

REFERENCES

1. Gould, P. L. Salt selection for basic drugs. *Int. J. Pharm.* 1986, 33 (1), 201-217.
2. Semin, D. J.; Jona, J.; Peterson, M. L.; Zanon, R. Salt screening and selection. *Burger's Medicinal Chemistry and Drug Discovery*, 2010, 381-400.
3. Bastin, R. J.; Bowker, M. J.; Slater, B. J. Salt selection and optimisation procedures for pharmaceutical new chemical entities. *Org. Process Res. Dev.* 2000, 4 (5), 427-435.
4. Elder, D. P.; Snodin, D. J. Drug substances presented as sulfonic acid salts: overview of utility, safety and regulation. *J. Pharm. Pharmacol.* 2009, 61 (3), 269-278.
5. Sarma, B.; Chen, J.; Hsi, H.-Y.; Myerson, A. S. Solid forms of pharmaceuticals: polymorphs, salts and cocrystals. *Korean J. Chem. Eng.* 2011, 28 (2), 315-322.
6. Shamshina, J. L.; Kelley, S. P.; Gurau, G.; Rogers, R. D. Chemistry: develop ionic liquid drugs. *Nature* 2015, 528 (7581), 188-189.
7. Rogers, R. D.; Seddon, K. R. Ionic liquids—solvents of the future? *Science* 2003, 302 (5646), 792-793.
8. Seddon, K. R. A taste of the future. *Nat. Mater.* 2003, 2 (6), 363-365.
9. Hough, W. L.; Smiglak, M.; Rodríguez, H.; Swatloski, R. P.; Spear, S. K.; Daly, D. T.; Pernak, J.; Grisel, J. E.; Carliss, R. D.; Soutullo, M. D.; Davis, J. J. H.; Rogers, R. D. The third evolution of ionic liquids: active pharmaceutical ingredients. *New J. Chem.* 2007, 31 (8), 1429-1436.
10. Balk, A.; Holzgrabe, U.; Meinel, L. 'Pro et contra' ionic liquid drugs—challenges and opportunities for pharmaceutical translation. *Eur. J. Pharm. Biopharm.* 2015, 94, 291-304.

11. Balk, A.; Wiest, J.; Widmer, T.; Galli, B.; Holzgrabe, U.; Meinel, L. Transformation of acidic poorly water soluble drugs into ionic liquids. *Eur. J. Pharm. Biopharm.* 2015, 94, 73-82.
12. Dobler, D.; Schmidts, T.; Klingenhöfer, I.; Runkel, F. Ionic liquids as ingredients in topical drug delivery systems. *Int. J. Pharm.* 2013, 441 (1), 620-627.
13. Ferraz, R.; Branco, L. C.; Prudêncio, C.; Noronha, J. P.; Petrovski, . Ionic liquids as active pharmaceutical ingredients. *ChemMedChem* 2011, 6 (6), 975-985.
14. Kumar, V.; Malhotra, S. V. Ionic liquids as pharmaceutical salts: a historical perspective. *Ionic Liquid Applications: Pharmaceuticals, Therapeutics, and Biotechnology, ACS Symposium Series* 2010, 1038, 1-12.
15. Marrucho, I. M.; Branco, L. C.; Rebelo, L. P. N. Ionic liquids in pharmaceutical applications. *Annu. Rev. Chem. Biomol. Eng.* 2014, 5 (1), 527-546.
16. Stoimenovski, J.; MacFarlane, D. R.; Bica, K.; Rogers, R. D. Crystalline vs. ionic liquid salt forms of active pharmaceutical ingredients: a position paper. *Pharm. Res.* 2010, 27 (4), 521-526.
17. Davis, J. H.; Forrester, K. J.; Merrigan, T. Novel organic ionic liquids (OILs) incorporating cations derived from the antifungal drug miconazole. *Tetrahedron Lett.* 1998, 39 (49), 8955-8958.
18. Monti, D.; Egiziano, E.; Burgalassi, S.; Chetoni, P.; Chiappe, C.; Sanzone, A.; Tampucci, S. Ionic liquids as potential enhancers for transdermal drug delivery. *Int. J. Pharm.* 2017, 516 (1), 45-51.
19. Babighian, S. Medical antiglaucomatous therapy. *Glaucoma Surgery, Springer* 2018; 97-98.
20. Flocks, M.; Zweng, H. C. Studies on the mode of action of pilocarpine on aqueous outflow. *Am. J. Ophthalmol.* 1957, 44, 380-386.
21. Skaat, A.; Rosman, M. S.; Chien, J. L.; Mogil, R. S.; Ren, R.; Liebmann, J. M.; Ritch, R.; Park, S. C. Effect of pilocarpine hydrochloride on the schlemm canal in healthy eyes and eyes with open-angle glaucoma. *JAMA Ophthalmol.* 2016, 134 (9), 976-981.
22. Yuan, Q.; Fu, Y.; Kao, W. J.; Janigro D.; Yang, H. Transbuccal delivery of CNS therapeutic nanoparticles: synthesis, characterization, and in vitro permeation studies. *ACS Chem. Neurosci.* 2011, 2, 676-683.
23. Katayanagi, H.; Nishikawa, K.; Shimozaki, H.; Miki, K.; Westh, P.; Koga, Y. Mixing schemes in ionic liquid-H$_2$O systems: a thermodunamic study. *J. Phys. Chem. B* 2004, 108, 19451-19457.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein; however, other combinations of steps, elements, components, and constituents are included, even though not explicitly stated.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A compound of Formula I

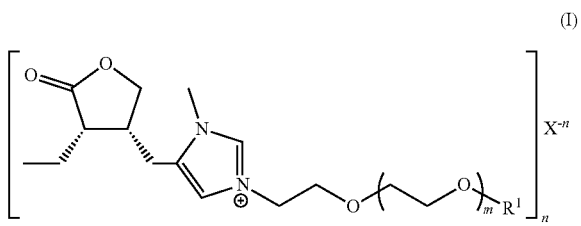

wherein:

R$^1$ is selected from hydrogen or C$_1$-C$_4$ alkyl;

m is 1, 2, 3, 4, 5, 6, 7, 8, 9, 10, 11, 12, 13, 14, 15, 16, 17, 18, 19, or 20;

X$^{-n}$ is a suitable anion having a charge of −n; and n is 1, 2, or 3.

2. The compound of claim 1, wherein R$^1$ is hydrogen.

3. The compound of claim 1, wherein m is 1, 2, 3, 4, or 5.

4. The compound of claim 1, wherein m is 2.

5. The compound of claim 1, wherein X$^{-n}$ is an anion selected from the group consisting of chloride, bromide, sulfate, hydrogen sulfate, sulfamate, phosphate, monohydrogen phosphate, dihydrogen phosphate, nitrate, acetate, propionate, succinate, glycolate, stearate, lactate, salicylate, mesylate, esylate, besylate, sulfanilate, 2-acetoxybenzoate, fumarate, toluenesulfonate, methanesulfonate, ethane disulfonate, oxalate, isethionate, malonate, glutarate, and adipate.

6. The compound of claim 1, wherein X$^{-n}$ is chloride.

7. The compound of claim 1, wherein the compound is of the formula

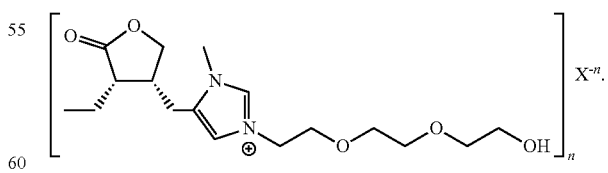

8. The compound of claim 7, wherein X$^{-n}$ is an anion selected from the group consisting of chloride, bromide, sulfate, hydrogen sulfate, sulfamate, phosphate, monohydrogen phosphate, dihydrogen phosphate, nitrate, acetate, propionate, succinate, glycolate, stearate, lactate, salicylate, mesylate, esylate, besylate, sulfanilate, 2-acetoxybenzoate, fumarate, toluenesulfonate, methanesulfonate, ethane disulfonate, oxalate, isethionate, malonate, glutarate, and adipate.

9. The compound of claim 1, wherein the compound is

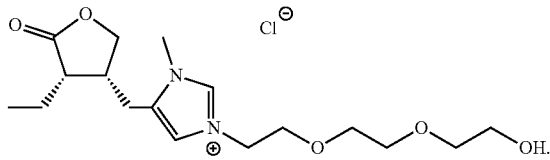 [SMILES: CC[C@@H]1C(=O)OC[C@@H]1Cc1c[n+](CCOCCOCCO)cn1C ; [Cl-]]

10. An ophthalmological composition comprising a compound of claim 1 and an ophthalmologically suitable carrier.

11. The ophthalmological composition of claim 10, wherein the compound is

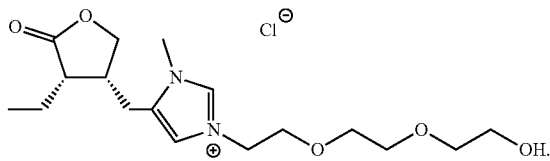 [SMILES: CC[C@@H]1C(=O)OC[C@@H]1Cc1c[n+](CCOCCOCCO)cn1C ; [Cl-]]

12. The ophthalmological composition of claim 10, wherein the composition is suitable for topical application to the eyes.

13. The ophthalmological composition of claim 10, wherein the composition comprises eye drops.

14. The ophthalmological composition of claim 10, further comprising one or more additional anti-glaucoma therapeutics.

15. The ophthalmological composition of claim 14, wherein the one or more additional anti-glaucoma therapeutics are selected from the group consisting of latanoprost, bimatoprost, travoprost, tafluprost, timolol, levobunolol, betaxolol, carteolol, metipranolol, brimonidine, apraclonidine, epinephrine, echothiophate, dorzolamide, brinzolamide, methazolamide, and acetazolamide.

16. A method of treating glaucoma in a subject in need thereof comprising administering to the subject a therapeutically effective amount of a compound of claim 1.

17. The method of claim 16, wherein the subject is a human.

18. The method of claim 16, wherein the compound is

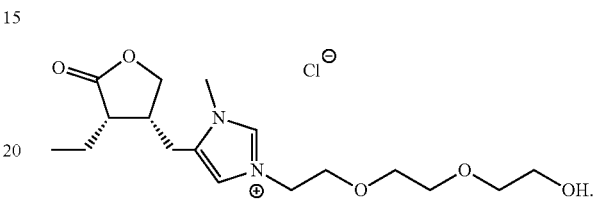

19. The method of claim 16, wherein the glaucoma is primary glaucoma, secondary glaucoma, open-angle glaucoma, or closed-angle glaucoma.

20. The method of claim 16, wherein the compound is administered in combination or alternation with an anti-glaucoma therapeutic selected from the group consisting of latanoprost, bimatoprost, travoprost, tafluprost, timolol, levobunolol, betaxolol, carteolol, metipranolol, brimonidine, apraclonidine, epinephrine, echothiophate, dorzolamide, brinzolamide, methazolamide, and acetazolamide.

* * * * *